Figure 1A:
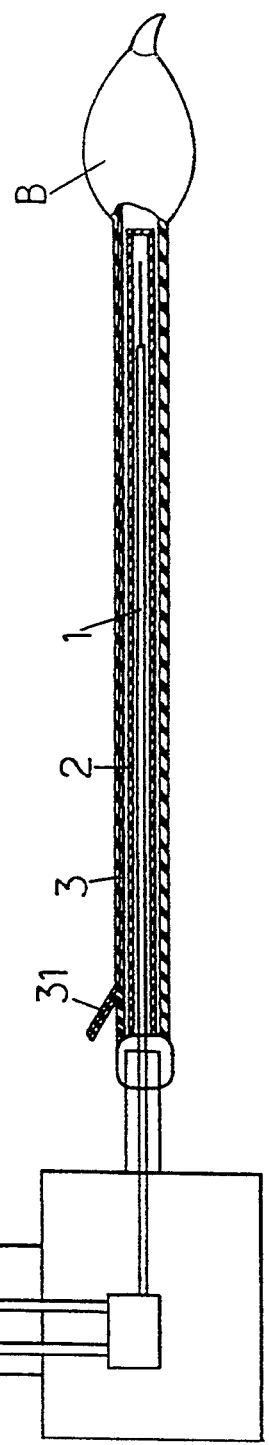

United States Patent [19]

Sozanski et al.

[11] Patent Number: 5,370,676
[45] Date of Patent: Dec. 6, 1994

[54] DEVICE FOR APPLICATION OF HYPERTHERMIA IN A PARTICULAR BODY USING MICROWAVES

[75] Inventors: Jean-Pierre Sozanski, Thumeries; Maurice Chive, Villeneuve d'Ascq; Yves Moschetto, Ennetieres en Weppes, all of France

[73] Assignees: Institut National de la Sante et de la Recherche Medicale, Paris; Universite des Sciences et Technologies de Lille, Villeneuve d'Ascq Cedex, both of France

[21] Appl. No.: 46,862

[22] Filed: Apr. 8, 1993

[30] Foreign Application Priority Data

Apr. 8, 1992 [FR] France .................... 92 04298

[51] Int. Cl.⁵ ............................. A61N 5/02
[52] U.S. Cl. ............................. 607/101; 607/102; 607/105; 607/113; 607/156; 128/642
[58] Field of Search ............ 607/99, 100, 101, 102, 607/104, 105, 113, 116, 154, 156; 128/639, 642

[56] References Cited

U.S. PATENT DOCUMENTS

| | | | |
|---|---|---|---|
| 4,662,383 | 5/1987 | Sogawa et al. | 607/156 |
| 4,823,812 | 4/1989 | Eshel et al. | 607/156 |
| 5,057,106 | 10/1991 | Kasevich et al. | 607/122 |
| 5,220,927 | 6/1993 | Astrahan et al. | 607/143 |
| 5,234,004 | 8/1993 | Hascoet et al. | 607/113 |

FOREIGN PATENT DOCUMENTS 0370890  5/1990  European Pat. Off.
0462302  12/1991  European Pat. Off.

*Primary Examiner*—Lee S. Cohen
*Assistant Examiner*—Brian M. Green
*Attorney, Agent, or Firm*—Larson and Taylor

[57] ABSTRACT

The invention relates to a device for application of hyperthermia in a particular body using microwaves. The device comprises a wire antenna (1) supplied with microwave energy or, upon switching, acting as a radiometric probe, a sleeve (2) enabling the wire antenna to be thermostatted and a Foley-type catheter (3) removably mounted so as to encompass the assembly thus constituted, the catheter enabling this assembly to be positioned in relation to an opening for insertion into the particular body and being the sole disposable part in order to ensure good hygiene of the hyperthermia session. A connection module (4) allows the interconnection both of the wire antenna, from the radio-frequency point of view, and of the sleeve and the catheter, from the hydraulic point of view. Application to thermotherapy or to the thermal treatment of certain bodies is thus provided.

25 Claims, 4 Drawing Sheets

U.S. Patent    Dec. 6, 1994    Sheet 1 of 4    5,370,676

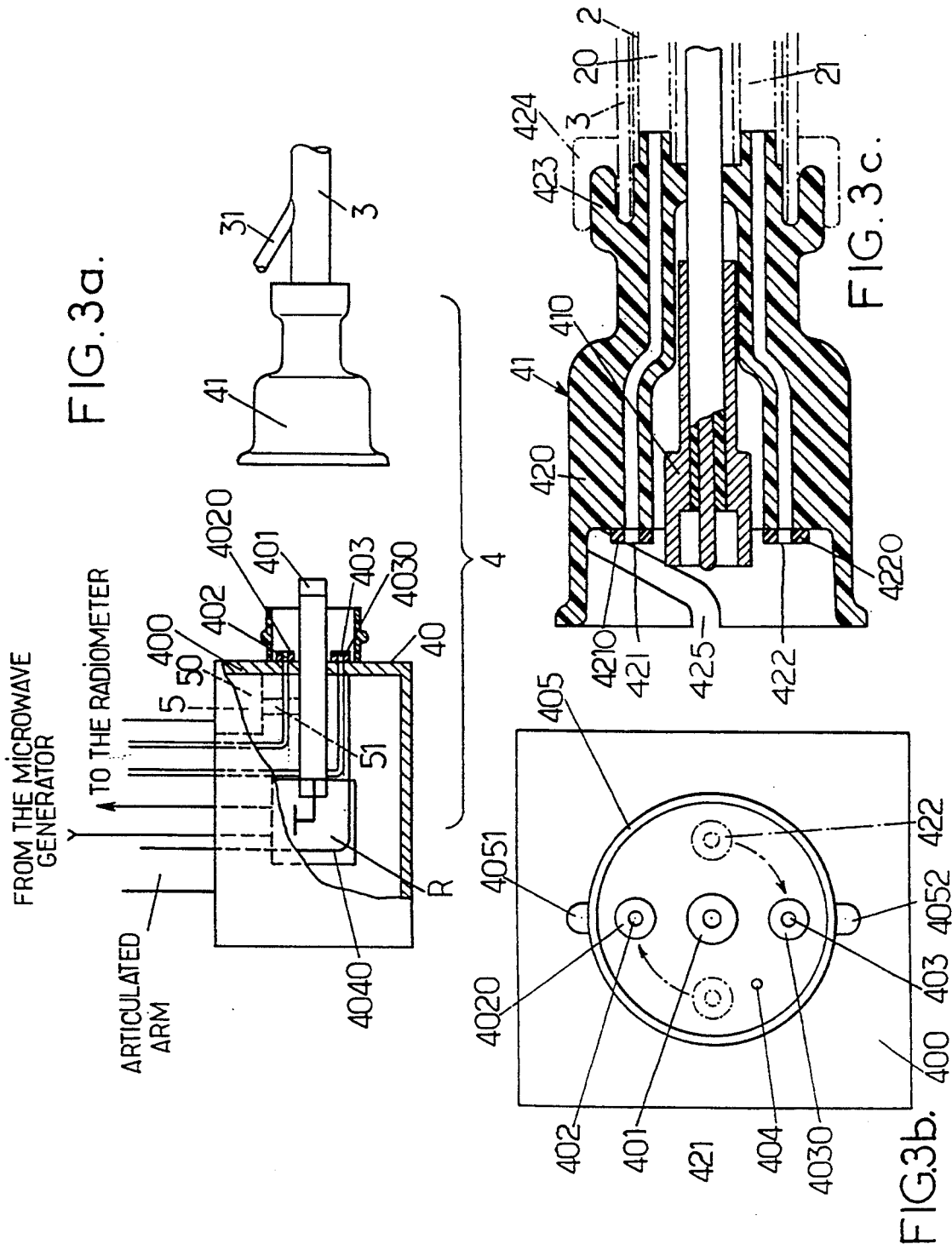

DEVICE FOR APPLICATION OF HYPERTHERMIA IN A PARTICULAR BODY USING MICROWAVES

The present invention relates to a device for application of hyperthermia in a particular body using microwaves.

Microwave hyperthermia applicators are currently used in thermotherapy, for example for treating adenoma of the prostate.

In such a case, a Foley-type catheter, that is to say a catheter including an inflatable positioning balloon, is inserted into the patient's urethra, positioning being carried out by inflating the balloon, these catheters having necessarily to combine functions of cooling the catheter, with a view to stabilising the surrounding walls of the tissues to be treated, and of measuring the corresponding temperatures.

After using a catheter under the aforementioned conditions, the latter has to be either thrown away or sterilized, with a view to being used again. The latter operation, of sterilization, cannot be performed easily since, on account of the complexity of current catheters, the aforementioned sterilization operation is liable to damage them, in particular in the case of delicate elements intended to measure the temperature which is associated with them. As a consequence, a non-negligible loss results therefrom, the practitioners and personnel using these types of catheter preferring, for obvious safety reasons, to dispose of the aforementioned catheters after their first use.

The object of the present invention is to overcome the aforementioned drawbacks by the implementation of a device for application of hyperthermia in which, although a conventional catheter is used, the functions of temperature measurement and of thermostatting (or cooling) of the catheter and the applicator antenna are completely separate from this catheter.

One subject of the present invention, taking into account the separation of the aforementioned functions from the actual catheter function, is also the implementation of a device for application of hyperthermia using a particularly simple and inexpensive catheter.

Another subject of the present invention is also the use, in the device for application of hyperthermia according to the invention, of a removable catheter which, taking into account the simplicity of the catheter used, enables it to be disposed of without difficulty after it has been used one or more times.

Finally, another subject of the present invention, taking into account the separation of the functions, is the implementation of a programmable reciprocating and/or rotary motion of the hyperthermia applicator catheter in the removable catheter so as to increase the heating zone and/or to modulate the thermal treatment dose.

The device, subject of the present invention, for application of hyperthermia in a particular body using microwaves comprises a wire antenna supplied with microwave energy or, upon switching, acting as a radiometric receiving probe for measuring temperature using microwave radiometry. It is noteworthy in that it includes a sleeve enabling the wire antenna to be thermostatted by means of a thermostatting fluid. A Foley-type catheter is removably mounted so as to encompass the assembly thus formed in relation to an opening for insertion into the particular body. A connection module is provided, this module allowing the interconnection both of the wire antenna, from the radio-frequency point of view, and of the sleeve and the catheter, from the hydraulic point of view.

The device, subject of the present invention, for application of hyperthermia using microwaves finds application not only in thermotherapy but also, much more generally, in the controlled thermal treatment of certain bodies.

Figure 2A:
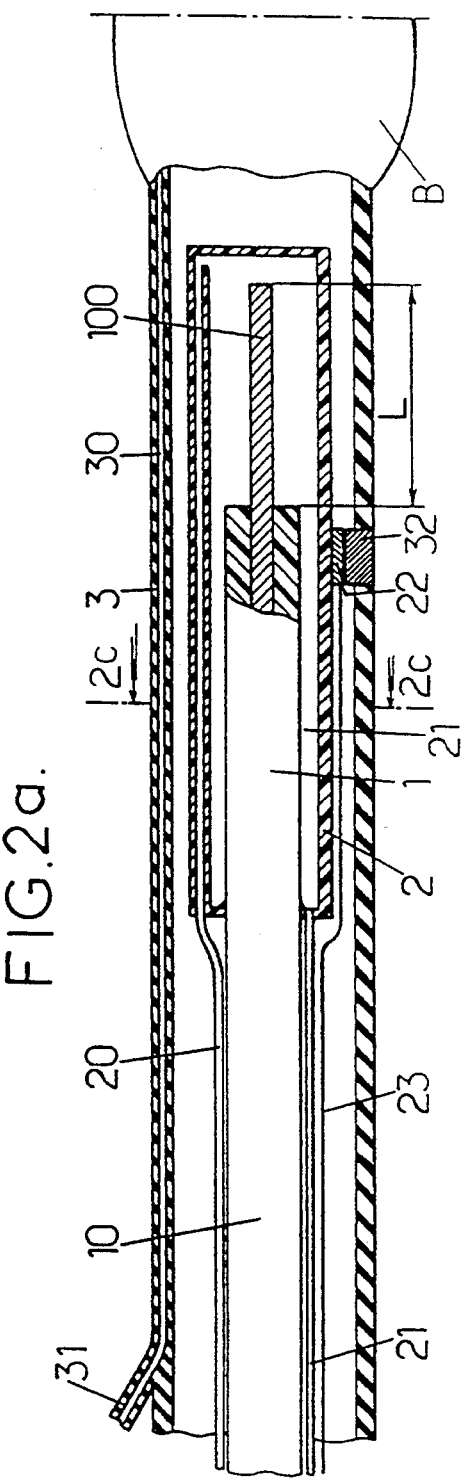
Figure 1B:
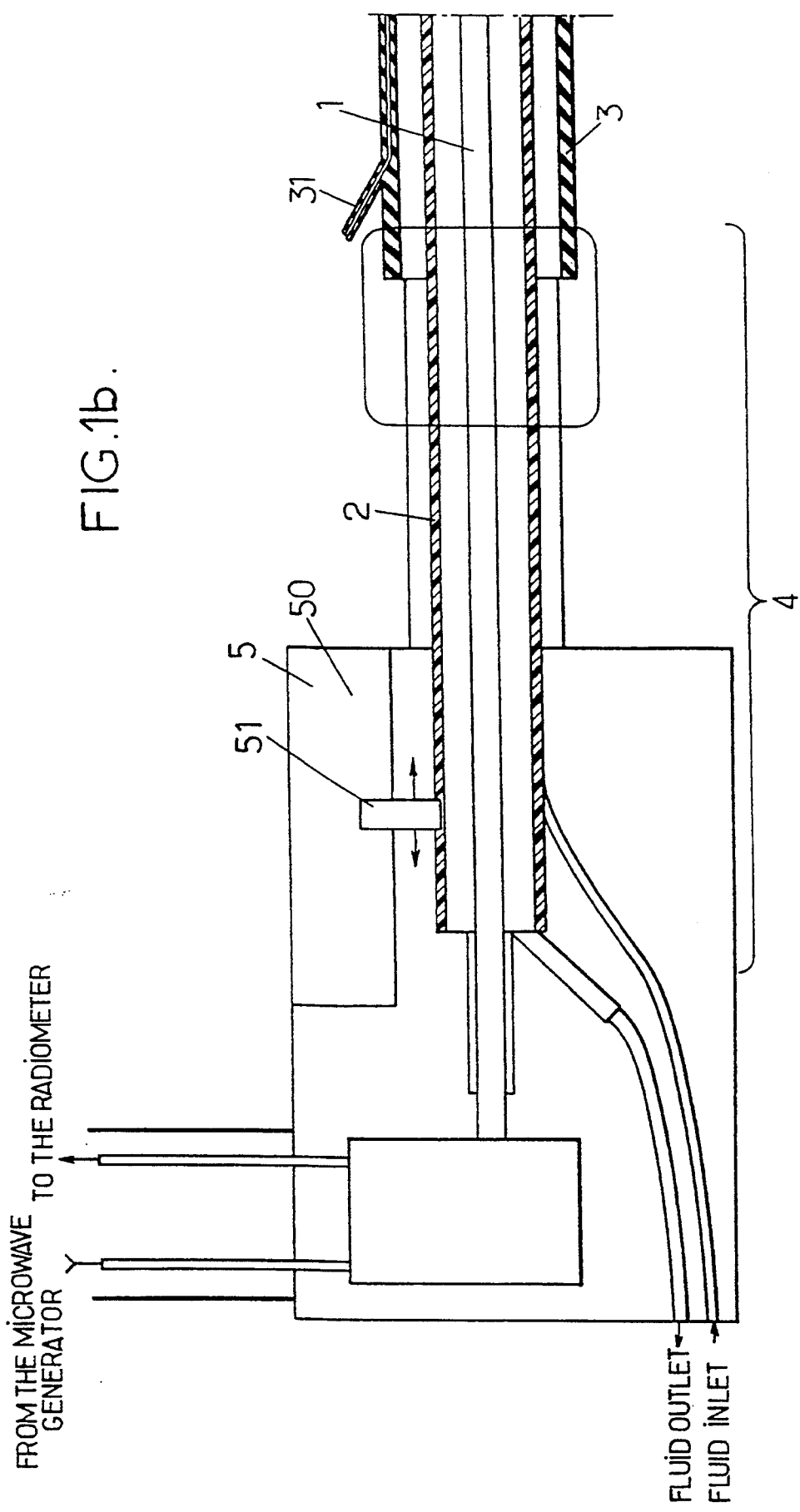
Figure 2B:
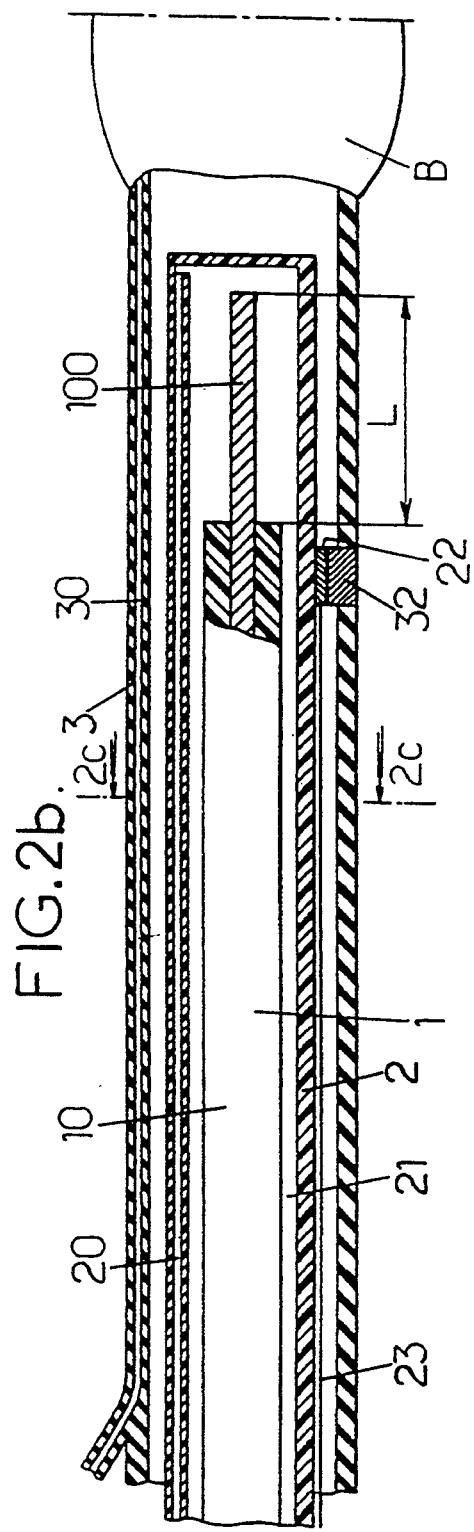
Figure 2C:
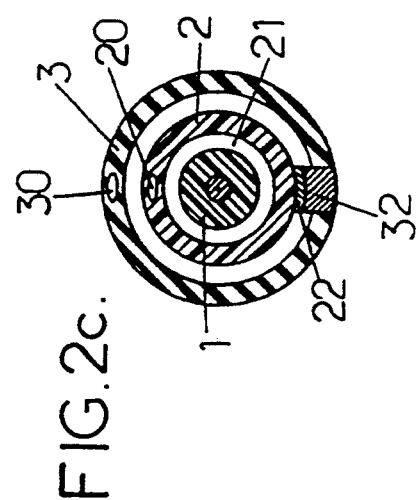

A more detailed description of the microwave hyperthermia applicator, the subject of the present invention, will be given hereinbelow with the aid of the drawings in which:

FIG. 1a represents, in a partial longitudinal sectional view, the hyperthermia applicator device, FIG. 1b represents, in partial longitudinal section, the hyperthermia applicator device combined with a reciprocating device with a view to modulating the thermal treatment dose, FIG. 2a represents, in a partial longitudinal sectional view, a first embodiment of an applicator device according to the invention, FIG. 2b represents, in a partial longitudinal sectional view, a second embodiment of an applicator device according to the invention, FIG. 2c represents a sectional view in the cutting plane 2c—2c of the embodiment shown in FIG. 2a or 2b, FIG. 3a represents an implementation variant of a connection module particularly adapted to the production of the applicator device which is the subject of the present invention, FIG. 3b represents a front view of a male connection element which is a constituent of the connection module shown in FIG. 3a, FIG. 3c represents a longitudinal sectional view of a female connection element which is a constituent of the connection module shown in FIG. 3a.

The device, the subject of the present invention, for application of hyperthermia using microwaves will be described in more detail in the first instance in connection with FIG. 1a.

In the aforementioned figure, it may be noted, by looking at the latter, that the device, the subject of the present invention, for application of hyperthermia using microwaves comprises a wire antenna, denoted 1, supplied with microwave energy or, upon switching, acting as a radiometric receiving probe for measuring temperature using microwave radiometry. Additional information relating to the aforementioned switching will be given later in the description, although the actual switching does not form part of the subject of the present invention.

As is apparent, by looking at FIG. 1a, the device according to the invention includes a sleeve 2 enabling the wire antenna 1 to be thermostatted by means of a thermostatting fluid. It will be noted that the thermostatting fluid may be constituted by water for example, or by a non-corrosive heat-transfer fluid, such as silicone oil for example.

The device, the subject of the present invention, for application of hyperthermia using microwaves furthermore includes a Foley-type catheter 3 removably mounted so as to encompass the assembly formed by the sleeve 2 and the wire antenna 1. Conventionally, the catheter 3 comprises a balloon B at the end of the catheter, it being possible for this catheter to be constituted, for example, by a beaked catheter, that is to say including an incurvate end, and a connection point 31 connected to a pump, not shown in the drawing, so as to inflate the balloon B by means of a duct, not shown in FIG. 1. Thus, conventionally, the catheter 3 enables the assembly thus formed to be positioned in relation to an opening for insertion of the aforementioned assembly into the particular body.

Furthermore, the device, the subject of the present invention, for application of hyperthermia using microwaves comprises a connection module 4 allowing the interconnection both of the wire antenna 1, from the radio-frequency point of view, and of the sleeve 2 and the catheter, from the hydraulic point of view.

A device or module 5 for driving the sleeve 2 may be provided, which enables a programmable reciprocating motion of the sleeve 2 in the catheter 3 to be carried out. This movement may be programmed as a function of time (modulation of the thermal dose) and/or as a function of the route (length and positioning of the scanning carried out). The drive module 5 may be constituted, for example, by a programmable stepping motor 50 enabling, by virtue of a drive rod 51, to subject the flexibly-mounted sleeve 2 and antenna, that is to say the radiating end of the latter, to a reciprocating translational motion, which enables the hyperthermia dose or degree of hyperthermia which is applied to be modulated. The amplitude of the motion is from 2 to 4 cm for example and, in addition, can be regulated in terms of time.

It will be recalled that, generally, the Foley-type catheter 3 may be, for example, a conventional rubber catheter, while the sleeve 2 enabling the antenna to be thermostatted may be a flexible cylindrical tube made from a PVC- or nylon-type material, the length of the flexible cylindrical tube constituting the sleeve then being a function of the active part of the antenna.

Furthermore, the device, the subject of the present invention, for application of hyperthermia using microwaves comprises a connection module 4 allowing the interconnection both of the wire antenna 1, from the radio-frequency point of view, and of the sleeve and the catheter, from the hydraulic point of view. Of course, it will be noted that the connection module 4 allows the interconnection of the wire antenna 1 towards the circuits coming from the microwave generator and, on the other hand, towards the circuits going towards a radiometer, in accordance with the operating mode previously described, for example, in French Patent Application No. 89/10148 in the name of the Applicant Company.

A first embodiment of the device, the subject of the present invention, will be described in connection with FIG. 2a.

FIG. 2a represents a longitudinal sectional view, which is a partial view, of the device, the subject of the present invention.

It will be noted that, generally, the wire antenna 1 is constituted by a coaxial cable 10, the end constituting the radiating end 100 of which is stripped over a length L which depends on the frequency of the microwave energy chosen for the heating. By way of non-limiting example, the length L may be taken to be equal to approximately 4 cm for a frequency of 915 MHz.

According to FIG. 2a, the sleeve 2 is then a short sleeve covering at most the coaxial cable 10 at its end over a length not exceeding 3 times the stripped length L. It will then be noted that the end of the sleeve 2 which is opposite the radiating end of the wire antenna may then be advantageously sealed, by adhesive bonding by means of an Araldite resin for example, to the jacket of the coaxial cable 10 so as to render leaktight the thermostatted zone formed by the interior of the sleeve 2.

By contrast, according to the embodiment of FIG. 2b, the sleeve 2 is constituted by a long sleeve covering the whole coaxial cable 10 over the entire length of the latter right up to the interconnection module 4, as will be described later in the description. In both cases, that is to say in the case of the embodiment of FIG. 2a or 2b, the sleeve 2 is constituted by a tube made from a dielectric plastic, as mentioned previously, this tube including, in its lateral wall, at least one elongate hole 20 acting as a duct for inlet of the hydraulic thermostatting fluid. The hydraulic fluid returns via the gap 21 existing between the coaxial cable 10 and the inner wall of the sleeve 2.

It will be noted in the case where the constituent tube of the sleeve 2 is a cylindrical tube, the elongate hole 20 is made along a line which is a generatrix of the wall of the aforementioned tube, so as to join up with the radiating end 100 of the wire antenna.

It will also be noted that, in the case where the sleeve is a short sleeve, as shown in FIG. 2a, the elongate hole 20 is extended beyond the sleeve, that is to say beyond the end sealed to the jacket of the coaxial cable 10, by means of a duct constituted by a plastic tube 20 which extends the aforementioned elongate hole 20 and, for this reason, bears the same reference.

The same is true for the gap 21 which is advantageously extended by a tube 21, the tube 21 and the tube 20 acting respectively as ducts for the return of thermostatting fluid and for the inlet of this same fluid. The tubes 20 and 21 may then be advantageously fixed by adhesive bonding to the jacket of the coaxial cable, for example. It will be noted that the plastic tubes 20 and 21 extending the corresponding elongate holes may advantageously be tubing of approximately 0.5 mm internal diameter and of 0.8 mm external diameter.

Thus, as has furthermore been shown in FIGS. 2a and 2b, the sleeve 2 may advantageously comprise, on its outer wall in the vicinity of the radiating end 100 of the wire antenna, a thermocouple cell 22 making it possible to measure the outer temperature of the wall of the particular body to be treated. Of course, a connecting wire 23 then enables the thermocouple cell 22 to be connected to the connection module 4 so as to enable the signal delivered by the thermocouple cell 22 to be picked up and thus the corresponding temperature to be measured.

In order to carry out a reliable temperature measurement of the wall of the particular body to be treated, the Foley-type catheter 3 may comprise, as shown in FIGS. 2a and 2b, throughout the thickness of its inner wall and in the vicinity of its end, that is to say of the balloon B, a thermal bridge 32. This thermal bridge is intended, after the catheter has been installed on the sleeve, to come into direct contact with the thermocouple cell 22 placed on the outer wall of the sleeve 2.

The thermal bridge 32 may be produced, for example, in the form of a pad of thermosetting resin filled with heat-conducting metal particles. The metal particles may be constituted by electrolytic-copper or silver particles.

FIG. 2c shows a sectional view, in the cutting plane 2c—2c of FIGS. 2a and 2b, of the device, the subject of the present invention, for application of hyperthermia using microwaves. In the aforementioned FIG. 2c, the substantially concentric arrangement of the wire antenna 1, constituted by the coaxial cable 10 of the sleeve 2, and then of the catheter 3 can be seen. Regarding the overall dimensions of the various aforementioned constituent elements, it will be recommended that the coaxial cable 10, that is to say the cable fitted with its dielectric jacket in the non-stripped part and with an outer electrostatic screen shield plus, where necessary, with a layer for protecting the latter using a plastic film, has a diameter of between 2.5 to 3 mm, the sleeve 2 has a diameter of the order of 4 to 5 mm and, finally, the catheter 3 has an outer diameter less than 9 mm. It may furthermore be recommended that the wall of the sleeve 2, when the latter is constituted by a silicone material for example, may have a thickness between 0.5 mm and 1 mm.

As regards the catheter 3, it will be noted that various sizes of catheter may be used and, in particular, catheters of 5.7; 6; 6.3 mm outer diameter corresponding to the standards designated by the names "French 17, French 18 and French 19".

A more detailed description of the connection module 4 will now be given in conjunction with FIGS. 3a to 3c.

According to the aforementioned FIG. 3a, the connection module 4 advantageously comprises a male connection unit 40 forming a connection case. The male connection unit 40 includes, on one face 400 of the case, a first microwave connector 401, intended to interconnect the wire antenna 1, and a second connector 402, intended to interconnect the conduit for inlet of the hydraulic thermostatting fluid, and a third connector 403, intended on the other hand to interconnect the conduit for return of the thermostatting fluid. The male connection unit 40 furthermore includes corresponding supply circuits inside the case.

It will be recommended, by way of non-limiting example, that the first radio-frequency connector 401 may be connected, towards the circuits coming from the microwave generator on the one hand and towards a radiometer circuit on the other hand, by an ultrahigh-frequency low-loss microwave relay enabling the applicator antenna to switch either towards the heating generator or towards the radiometer. The embodiment of the interconnection of the first microwave connector 401, towards the generator or towards the radiometer, does not form part of the subject of the present invention.

As FIG. 3a furthermore shows, the connection module 4 comprises a female connection element, denoted 41, which is rigidly attached to the catheter, to the sleeve and to the coaxial cable forming the wire antenna. Of course, it is understood that the male or female qualifier reserved for the connection element 40 or 41 respectively, may be inverted without departing from the scope of the subject of the present invention.

In general, the first microwave connector 401 may be an independent lockable connector. The second 402 and the third 403 connectors of the male connection element 40 may then advantageously be constituted by connection orifices arranged symmetrically in relation to the central axis of the first microwave connector 401. It will then be noted that the constituent connection orifices of the second 402 and third 403 connectors are fitted with leaktight seals 4020, 4030, which are conventionally constituted by sealing rings of the O-ring type.

FIG. 3b thus shows a view of the face 400 of the constituent case of the male connection unit 40, this face 400 including, respectively, the first radio-frequency connector 401 in the central position, the second 402 and the third 403 connectors formed by the corresponding orifices and their leaktight seals 4020, 4030. Furthermore, the existence will be noted in the position intermediate in relation to the second and third connectors 402, 403, of a terminal 404 of the electrical terminal type, which is connected by a conducting element 4040 towards the processing circuits, this contact terminal 404 being intended to receive the contact of a corresponding element placed in the female connection element 41 and connected, for example, to the connecting wire 23 with the thermocouple cell 22. The latter elements will not be shown in the drawing so as not to clutter up the latter unnecessarily.

Finally, it will be noted that the connection unit 40 furthermore comprises, on the aforementioned face 400, an outer circular ring, denoted 405, centered on the first radio-frequency connector 401 and fitted with two diametrically-opposed pins denoted 4051, 4052. The collar 405 and the pins 4051, 4052 are intended to receive and to interconnect the male connection unit 40 with the female connection element 41, as will be described hereinbelow in conjunction with the aforementioned FIG. 3b and with FIG. 3c.

According to the aforementioned FIG. 3c, the connection module 4 also comprises a female connection element 41, this element including a first female connector, denoted 410, constituted by a radio-frequency connector and intended to interconnect the wire antenna 1 and the coaxial cable 10 with the radio-frequency connector 401.

Furthermore, as may be seen in the aforementioned FIG. 3c, the female connection element 41 includes a second female connector 420 which is coaxial with the first 410 and is intended to interconnect, respectively, the inlet conduit 20 and the return conduit 21 for the hydraulic thermostatting fluid respectively with the second connector 402 and third connector 403 of the male connection unit 40.

By way of non-limiting example, it will be recommended that the first radio-frequency female connector 410 may be constituted by a metal body in which the coaxial cable 10 is conventionally mounted. By contrast, the second female connector 420 may, itself, be a plastic connector body, which is moulded for example. Thus, the contact terminal, not shown in FIG. 3c, intended to come into contact with the corresponding contact terminal 404 of the connection unit 40, may be connected directly by a wire embedded in the female connector body 41, but not shown in the drawing. It will be noted, by way of non-limiting example, that the body of the first female connector 410 and the body of the second female connector 420 are advantageously mounted so as to be free to slide and to rotate one in relation to the other. It will furthermore be noted that the body of the second female connector 420 includes orifices 421, 422 which are connected via corresponding channels to the rear part of the female connector body 41, the aforementioned orifices of course being fitted with leaktight seals 4210, 4220, for example constituted by O-ring seals, in the same manner as in the case of the male connector body 40. The orifices 421 and 422 are preferably located substantially symmetrically and diametrically opposed in relation to the longitudinal axis of the first female connector 410. Finally, it will be noted that the body of the second female connector 41 is also equipped with insertion and locking openings made on the wall of the female connector body 420 and bearing the reference 425. It will be noted that, in a particularly advantageous manner, these guiding and locking openings 425 are made in such a way that their opening on the edge of the collar forming the female connector body 41 is offset by a quarter of a turn in relation to the position of the corresponding orifices 421 and 422.

Thus, the first female connector 410 may be interconnected to the first male connector 401 by screwing, the second female connector 420 having been moved translationally so as to render the first female connector 410 visible and accessible, then, the catheter 3 having been installed on the rear part of the female connector 41, the second female connector 420 is then interconnected to the second 402 and the third 403 male connector by a rotation of a quarter of a turn. The respective leaktight seals 4210, 4220 are then brought by the rotation of a quarter of a turn into a position opposite the leaktight seals 4020 and 4030 respectively of the connection unit 40, as shown in FIG. 4b. The second female connector 420 is then fixed by means of the pins 4051, 4052 provided on the previously described collar 405.

In order to instal the catheter 3 correctly at the rear part of the female connector 420, the latter may advantageously include, on the outer face of the second female connector 420, a ring 423 for relative positioning and locking of the Foley-type catheter 3 in relation to the sleeve 2. Furthermore, a ring 424, for permanent fixing by screwing, may be provided so as to retain the catheter during the period of operation. Of course, it will be noted that the tubes 20 and 21, constituting the ducts respectively for the inlets and the return of the thermostatting fluid, may have been fixed beforehand to the rear part of the connector and of the second female connector 420, as shown in FIG. 3c.

Furthermore, it will be noted that, since the first female connector 410 is mounted so as to be free to move translationally, before connection, in the female connector body 41, the first microwave connector 401 of the connection element 40 may also be mounted so as to slide translationally, as it is connected to the microwave relay R via a flexible coaxial cable, which enables the drive module 5 to drive the assembly, it being possible for the sleeve to be a short sleeve.

A particularly high-performance device has thus been described for application of hyperthermia in a particular body using microwaves, insofar as the structure of this type of hyperthermia applicator makes it possible to separate the function of temperature measurement from the function of thermostatting the catheter and the applicator antenna, only a simple positioning function devolving to the Foley-type catheter used in the device, the subject of the present invention, which enables, after using the catheter, which has a particularly simple structure, the disposal of the latter after it has been used one or even more times to be envisaged.

Furthermore, it will be noted that the implementation of a particularly adapted interconnection module makes it possible to connect up permanently all the electrically and fluidic connections regarding the thermostatting fluid, which makes it possible, of course, to eliminate the "spaghetti" effect of the interconnections which is disliked by practitioners.

We claim:

1. A device for application of hyperthermia in a body using microwaves comprising:
   a wire antenna having a radiating end and a distal end;
   a sleeve surrounding said radiating end of said wire antenna with a space therebetween, the space having a fluid supply inlet and a fluid return outlet and being filled with a thermostatting fluid for thermostatting said wire antenna;
   a Foley-type catheter removably mounted about said wire antenna and said sleeve and including an inflation connection point by which said Foley-type catheter is connectable to an inflation pump, whereby said Foley-type catheter enables said wire antenna and said sleeve carried therein to be positioned in the body for application of hyperthermia and said Foley catheter is disposable so that said wire antenna and said sleeve are reusable; and
   a connection module including a male connection unit forming part of a connection case, said male connection unit having a face including (a) a first connector connected to said distal end of said wire antenna for connecting said distal end of said wire antenna selectively to a microwave generator or to a microwave radiometer, (b) a second connector connected to said fluid supply inlet for connecting said fluid supply inlet of said space to a thermostatting fluid supply, and (c) a third connector connected to said fluid return outlet for connecting said fluid return outlet of said space to a thermostatting fluid return.

2. The device as claimed in claim 1 wherein said wire antenna is a coaxial cable including a wire and a sheath; wherein said radiating end is a part of a proximal end of said coaxial cable distal from said distal end with said sheath stripped away for a length L; and wherein said sleeve covers said proximal end for a length along said coaxial cable not exceeding three times the stripped length L.

3. The device as claimed in claim 1 wherein said connection module further includes a programmable module for driving said sleeve and said wire antenna in motion relative to the surrounding said Foley-type catheter.

4. The device as claimed in claim 1 wherein said wire antenna is a coaxial cable including a wire and a sheath; wherein said radiating end is a part of a proximal end of said coaxial cable distal from said distal end with said sheath stripped away for a length L; and wherein said sleeve covers said coaxial cable from said proximal end to said distal end.

5. The device as claimed in claim 1 wherein said sleeve is a tube made from a dielectric material and having a lateral wall, at least one duct in said lateral wall connected to said fluid supply inlet, and said fluid return outlet is longitudinally spaced from said fluid supply inlet whereby the thermostatting fluid circulates in the space between said fluid supply inlet and said fluid return outlet.

6. The device as claimed in claim 5 wherein said tube is cylindrical, and wherein said duct is linear and extends longitudinally to said radiating end of said wire antenna.

7. The device as claimed in claim 1 and further including a thermocouple cell provided on an outer wall of said sleeve adjacent said radiating end of said wire antenna whereby a temperature of the body adjacent said thermocouple cell is measured.

8. The device as claimed in claim 7 wherein said Foley-type catheter includes a wall portion comprising a thermal bridge, said thermal bridge being positioned to be in direct contact with said thermocouple cell.

9. The device as claimed in claim 8 wherein said thermal bridge is formed by a pad of thermosetting resin filled with metal particles.

10. The device as claimed in claim 1 wherein said first connector is an independently lockable connector having a central longitudinal axis; and wherein said second connector and said third connector are each respective connection orifices provided with respective leaktight seals thereabout, said second and third connectors being arranged symmetrically about said longitudinal axis.

11. The device as claimed in claim 1 wherein said connection module further includes a female connection element rigidly attached to said Foley-type catheter, to said sleeve, and to said wire antenna, said female connection element including (a) a first female connector which connects said wire antenna to said first connector of said male connection unit, and (b) a second female connector and a third female connector which respectively connect said fluid supply inlet and said fluid return outlet to respective said second and third connectors of said male connection unit.

12. The device as claimed in claim 11 wherein said first female connector is interconnected to said first connector of said make connection unit by a screwing action while said second and third female connectors are interconnected to respective said second and third connectors of said male connection unit by a rotational action as said male connection unit is rotated a quarter of a turn relative to said female connection unit.

13. The device as claimed in claim 12 wherein said first female connection unit further includes an outer face and a ring on said outer face which relatively positions and locks said Foley-type catheter relative to said sleeve.

14. A device for application of hyperthermia in a body using microwaves during a hyperthermia session comprising:
a coaxial cable including a wire and a sheath which forms a wire antenna having a radiating end and a distal end, said radiating end being a part of a proximal end of said coaxial cable distal from said distal end with said sheath stripped away for a length L;
a sleeve surrounding said radiating end of said wire antenna with a space therebetween, the space having a fluid supply inlet and a fluid return outlet and being filled with a thermostatting fluid for thermostatting said wire antenna, said sleeve covering said proximal end for a length along said coaxial cable not exceeding three times the stripped length L;
a Foley-type catheter removably mounted about said wire antenna and said sleeve; and
a connection module which includes means for interconnecting (a) said distal end of said wire antenna selectively to a microwave generator or to a microwave radiometer, (b) said space to a thermostatting fluid supply, and (c) said Foley-type catheter to a pump, whereby said Foley-type catheter enables said wire antenna and said sleeve carried therein to be positioned in the body for application of hyperthermia and said Foley catheter is disposable so that said wire antenna and said sleeve are reusable.

15. The device as claimed in claim 14 wherein said connection module further includes a programmable module for driving said sleeve and said wire antenna in motion relative to the surrounding said Foley-type catheter.

16. The device as claimed in claim 14 wherein said sleeve is a tube made from a dielectric material and having a lateral wall, at least one duct in said lateral wall connected to said fluid supply inlet, and said fluid return outlet is longitudinally spaced from said fluid supply inlet whereby the thermostatting fluid circulates in the space between said fluid supply inlet and said fluid return outlet.

17. The device as claimed in claim 16 wherein said tube is cylindrical, and wherein said duct is linear and extends longitudinally to said radiating end of said wire antenna.

18. The device as claimed in claim 14 and further including a thermocouple cell provided on an outer wall of said sleeve adjacent said radiating end of said wire antenna whereby a temperature of the body adjacent said thermocouple cell is measured.

19. The device as claimed in claim 18 wherein said Foley-type catheter includes a wall portion comprising a thermal bridge, said thermal bridge being positioned to be in direct contact with said thermocouple cell.

20. The device as claimed in claim 19 wherein said thermal bridge is formed by a pad of thermosetting resin filled with metal particles.

21. The device as claimed in claim 14 wherein said connection module further includes a male connection unit forming part of a connection case, said male connection unit having a face including (a) a first connector connected to said distal end of said wire antenna for connecting with said distal end of said wire antenna, (b) a second connector connected to said fluid supply inlet for connecting with said fluid supply inlet, and (c) a third connector connected to said fluid return outlet for connecting with said fluid return outlet.

22. The device as claimed in claim 21 wherein said first connector is an independently lockable connector having a central longitudinal axis; and wherein said second connector and said third connector are each respective connection orifices provided with respective leaktight seals thereabout, said second and third connectors being arranged symmetrically about said longitudinal axis.

23. The device as claimed in claim 21 wherein said connection module further includes a female connection element rigidly attached to said Foley-type catheter, to said sleeve, and to said wire antenna, said female connection element including (a) a first female connector which connects said wire antenna to said first connector of said male connection unit, and (b) a second female connector and a third female connector which respectively connect said fluid supply inlet and said fluid return outlet to respective said second and third connectors of said male connection unit.

24. The device as claimed in claim 23 wherein said first female connector is interconnected to said first connector of said male connection unit by a screwing action while said second and third female connectors are interconnected to respective said second and third connectors of said male connection unit by a rotational action as said male connection unit is rotated a quarter of a turn relative to said female connection unit.

25. The device as claimed in claim 24 wherein said first female connection unit further includes an outer face and a ring on said outer face which relatively positions and locks said Foley-type catheter relative to said sleeve.

* * * * *